United States Patent [19]

Pedersen et al.

[11] Patent Number: 4,861,720

[45] Date of Patent: Aug. 29, 1989

[54] ONCORNAVIRUS VACCINES AND FELINE ALPHA-TYPE INTERFERON

[75] Inventors: Neils C. Pedersen, Winters; Janet Yamamoto, Woodland, both of Calif.

[73] Assignee: Regents of the University of California, Calif.

[21] Appl. No.: 882,088

[22] Filed: Jul. 3, 1986

[51] Int. Cl.$^4$ .................... C12N 7/06; A61K 39/21
[52] U.S. Cl. .................... 435/238; 424/89; 424/93
[58] Field of Search .................... 424/88–89, 424/93, 85, 93; 435/235, 238, 236, 239

[56] References Cited

U.S. PATENT DOCUMENTS

| | | | |
|---|---|---|---|
| 4,086,134 | 4/1978 | Jarrett et al. | 424/89 |
| 4,264,587 | 4/1981 | Pedersen | 435/238 |
| 4,699,785 | 10/1987 | Pedersen | 435/235 |

OTHER PUBLICATIONS

Chemical Abstracts, vol. 103, Abstract No. 140019h, 1983.
Chemical Abstracts, vol. 99, Abstract No. 20761w, 1983.
Chemical Abstracts, vol. 98, Abstract No. 158909m, 1983.
Chemical Abstracts, vol. 77, Abstract No. 86507v, 1972.
Chemical Abstracts, vol. 99, Abstract No. 156594b, 1983.

*Primary Examiner*—Blondel Hazel
*Attorney, Agent, or Firm*—Bertram I. Rowland; W. Murray Spruill

[57] ABSTRACT

Retroviral vaccines are provided comprising incompetent retroviruses containing defective RNA produced by growing viral transformed cells in the presence of interferon. The resulting defective viruses by themselves or in combination with interferon can be used as vaccines for immunizing viral sensitive hosts against infection. A novel feline interferon is produced in culture with cells infected with the defective non-infectious retroviruses.

9 Claims, No Drawings

ONCORNAVIRUS VACCINES AND FELINE ALPHA-TYPE INTERFERON

BACKGROUND OF THE INVENTION

1. Field of the Invention

Retroviruses are ubiquitous as pathogens for a wide variety of diseases. The etiology of many cancers are attributed to retroviruses. With the advent of molecular biological techniques, there has been increasing information about the manner in which retroviruses infect, replicate, and cause various disease states. Retroviruses are considered the causal agents of a wide variety of lymphocyte diseases, such as leukemias, lymphomas and T-lymphotropic diseases.

The retroviruses have a basic genetic structure, where the retrovirus has the genes referred to as gag, pol, and env, with frequently one or more additional open reading frames. For a variety of reasons, the retroviruses have proven to be less tractable than other viruses in providing for attenuated strains by passaging of the viruses. The retroviruses tend to be highly infectious and when mutations or lesions occur, two defective viral strains having different mutations may recombine to provide for a newly infectious virus.

There is a substantial interest in being able to provide for vaccines which would provide protection to a host susceptible to infection by the retrovirus. Some consideration has been given to using either individual viral proteins, combinations thereof, or fragments of such proteins or combinations thereof as immunogens. These approaches have only been recently initiated and it is still too early to say if they will provide for a satisfactory solution. In any event, these approaches do not provide the envelope or capsid in its native form, so it is not clear that a strong immune response will be obtained to the viral proteins in their native conformation. There is, therefore, substantial interest in developing vaccines which closely mimic the immunogenicity of the native virus, and have an insignificant probability of reverting to an infectious state.

2. Brief Description of the Relevant Literature

Armstrong, Applied Microbiology (1971) 21:723-725; DeStefano et al, J. Infect. Dis. (1982) 146:451-455; Montagnier et al. 1984, n: Human T-cell Leukemia-Lymphoma Viruses. Gallo, Essex and Gross (editors), Cold Springs Harbor, N.Y., 363-379, report the formation of an atypical interferon in people with systemic lupus erythematosus and acquired immune deficiency syndrome (AIDS). Yamamoto et al, Vet Immun. Immunopath. (1986) 11:1-19 report a feline retrovirus induced T-lymphoblastoid cell-line that produced an atypical alpha-type of interferon.

SUMMARY OF THE INVENTION

Novel vertebrate cell cultures are provided being characterized by being infected with defective oncornavirus in producing an atypical acid labile alpha-type interferon. The cells are T-lymphoblastoid cells obtained from a retroviral induced thymic tumor, which can be grown in culture to produce the atypical alpha-interferon and defective retrovirus, which can be used by itself or in combination with the alpha-interferon as a vaccine. The retrovirus is found to have defective RNA, while producing the primary proteins of the retrovirus.

DESCRIPTION OF THE SPECIFIC EMBODIMENTS

Normal retroviral infected cell lines, the defective viruses produced by such cell lines, and novel acid labile alpha-type interferons are provided. These cell lines are mammalian cell lines other than primate cell lines, such as feline, bovine, canine, or the like.

The cell lines are characterized by being T-lymphoblastoid cells infected with a retrovirus, where the cell lines are grown in the presence of an interferon, particularly an alpha-interferon, and more particularly an acid labile alpha-type interferon (alpha-interferon includes both the numerous alpha-interferons resulting from lymphocytes other than T-cells and referred to as alpha-interferon and alpha-type interferons as observed with some retroviral infected lymphocytes including T-cells). The interferon may be endogenously produced by the cell line or may be added to the cell culture in amounts of from about 100 to 5,000 units/ml. Except for the presence of the interferon in the medium, conventional media may be employed for growing immortalized lymphocytes such as combinations of Eagle's minimum essential media (Earle's base) and Leibowitz's-15 media with from 5 to 15% fetal serum; e.g. bovine. These cells can be commonly grown as suspensions in stationary culture flasks.

The cells may be obtained by inducing tumors in an appropriate host, generally a young host, of at least about eight weeks of age and commonly not more than about six months of age. The tumors are induced with a retrovirus known to induce a solid or a non-solid tumor, e.g. a sarcoma, more particularly, a fibrosarcoma.

The method may be illustrated by the infection of a young cat with infectious feline sarcoma virus, waiting for the locally induced fibrosarcoma to regress, after which time the cat becomes retroviremic with the helper virus, the feline leukemia virus, which is present in the feline sarcoma virus composition. At some time, the tumorous mass may be isolated and finely minced and placed into culture. The stable cell line may then be screened for the production of interferon and in those instances where the amount of interferon is less than about 50 units/ml, alpha-interferon may be augmented to provide for at least about 100 units/ml, preferably at least about 300 units/ml. The cell line may be grown until the immunogen level, particularly a core immunogen level, reaches a concentration of at least about 100ng/ml, preferably at least 200ng/ml. and more preferably at least about 300ng/ml. Usually the specific immunogen level used as the standard will not exceed about 10ng/ml.

The retrovirus will bud from the host cell and will have a substantially intact capsid including core and envelope proteins. The incompetent retrovirus may be isolated substantially free of cells, cellular debris, and proteins in the nutrient medium. The retrovirus may be isolated by harvesting the culture fluid in accordance with conventional ways, e.g. centrifugation, filtration or the like, and, if desired, concentrating the culture fluid.

For preparation of a vaccine, it is desirable that the tissue culture fluid be concentrated at least two-fold, preferably at least about four-fold, and more preferably at least about five-fold, usually not more than about ten-fold, by separating the virus particles from the fluid, e.g. ultracentrifugation, and then resuspending the virus particles with tissue culture fluid, so as to provide for at least a two-fold increase in concentration and preferably at least about a four-fold in concentration, more preferably at least about a five-fold increase in concentration. Normally, the tissue culture fluid will also include significant levels of alpha-interferon, which, while desirable, is not essential for the use of the virus as a vaccine. Usually the amount of interferon will be at least about 100 units/ml and not more than about 5,000 units/ml, generally ranging from about 300 to 3,000 units/ml.

The retroviral vaccine may be reconstituted for use by dilution with an appropriate physiologically acceptable medium, e.g. sterile distilled water, to provide for the appropriate volume concentration. Conveniently, the same volume which was lyophilized may be reconstituted, so that the original concentration will be recreated. Usually, about 0.5 to 2ml of the vaccine may be injected into the host, either intramuscularly or intraperitoneally (IP), preferably IP, which with babies would usually not be applied earlier than nine weeks, with one or more booster immunizations at three to four week intervals followed by annual immunizations. With young and mature hosts, a schedule of two or more immunizations may be employed, separated by about two to four weeks.

The defective virus is characterized by having defective RNA, demonstrated by having a substantially lower proportion of RNA of total composition, as compared to infectious analogues. Conversely, the virus appears to have a much higher proportion of protein based on the weight of the total composition as compared to infectious analogues.

The defective viruses are further characterized by being capable of producing capsid and envelope proteins associated with retroviruses, while being incapable of producing foci on feline cells, where the infectious analogues are capable of producing foci.

The electron micrographs of the non-infectious virus particles can be distinguished from the infectious particles, by the less dense appearance of the nucleoids and their generally smaller size. The retroviruses may be further distinguished in many instances by inducing the constitutive production of alpha-type interferon in lymphoblastoid cells.

The alpha-type interferon is characterized by being acid-labile (pH2, with HCl) while being sodium dodecylsulfate (0.1% SDS for 2h at r.t.) and heat stable (56° C. for 30 min.) For the feline alpha-type interferon, the molecular weight is about 20 KiloDaltons (kDal). The alpha-type interferon is found like standard alpha-interferons to supress mitogen induced blast cell responses of normal peripheral blood lymphocytes. In the case of the feline alpha-type interferon, there is some cross-reactivity between species, since the feline alpha-type interferon also reacts with MDCK canine cells.

The alpha-type interferon may be obtained by growing T-cells infected with FeLV which constitutively produce the alpha-type interferon in an appropriate nutrient medium. The alpha-type interferon may be purified on gel chromatographs employing 5% ethylene glycol in 1M phosphate buffered saline (pH7) to provide preparations having activities of at least about $1 \times 10^5$ units/mg, more usually at least about $1 \times 10^6$ units/mg, preferably at least about $5 \times 10^6$ units/mg, more preferably completely freed of the proteins normally found in conditioned media, and more preferably in complete purity (100%).

The alpha-type interferon may be used in the preparation of vaccines, not only for cats, but with other non-primate mammalian cells infected with C-type retroviruses, such as murine leukemia virus, gibbon-ape leukemia virus, woolly monkey sarcoma virus, and the like. Interferons other than alpha-type may be employed, such as alpha-interferons, beta-interferons and gamma-interferons, although the alpha or alpha-type interferons are preferred. Besides being used with C-type retroviruses, the interferons may be used with B-type retroviruses to provide for defective production of retroviruses, which may be used as vaccines, in diagnostics, or the like. The alpha-type interferon may also be used in conjunction with or by itself for therapy, much in the manner of the analogous alphainterferons. See, EPA Ser. No. 32,134, for example.

The vaccines will usually have the defective retroviruses formulated with a physiologically acceptable carrier which may be sterilized water, saline, phosphate buffered saline, excipients, adjuvants, buffers, or the like. The vaccine may be prepared in lyophilized form, but will usually be diluted prior to use in a physiologically acceptable liquid medium. The dose will usually include from about 500–5000ng/ml of a major core or envelope protein.

The following examples are offered by way of illustration and not by way of limitation.

EXPERIMENTAL

Cell Lines. Lymphosarcoma (LSA)-I cells were derived from a thymic tumor induced by Snyder-Theilen FeLV (ST-FeLV) in a 1 year old domestic feline. The cat was infected at 16 weeks of age with ST-feline sarcoma virus (ST-FeSV), and after the locally induced fibrosarcoma had regressed, it became persistently retroviremic with the helper virus (ST-FeLV) present in all ST-FeSV stocks (de Noronha et al., Cancer Res. (1983) 43:1663–1668; Pedersen et al., Infect. Immun. (1984) 43:631–636). Eight months later, the cat suddenly became dyspneic and was euthanitized. A large anterior mediastinal mass was identified at necropsy. The mass had the typical appearance of a thymic lymphosarcoma on histological examination. A small piece of the tumor was finely minced and placed into culture. Lymphoblastoid cells from the tumor grew free in the culture media, forming small clumps of 10 to 50 cells. These nonadherent cells were periodically passaged, and at the 5th passage they were assayed for lymphokine elaboration and aliquots of the cells were frozen in liquid nitrogen. These cells were designated LSA-I. The LSA-I cells were cloned at this time; LSA-D4 and -D5 clones produced high levels FeLV-p27 and interferon, while LSA-MA, -MC, -ME, -MG, -MI, and -MK clones produced high levels of FeLV-p27 but low levels of interferon. The LSA-I cell line and its clones were propagated in 50% Eagle's minimum essential media (Earle's base) and 50% Leibowitz's-15 (MEM/L15), media with 10% fetal bovine serum. The cells grew best as a suspension in stationary culture flasks.

The FL74 feline lymphoblastoid cell line was obtained originally from a cat with a FeLV induced renal lymphosarcoma (Theilen et al, *Nature* (1969) 272:589–590). This cell produces high levels of FeLV of subgroups A, B, and C (Sarma, et al., Virology (1973) 54:160-169). FF64/280 cells were primary feline fibroblasts that had been productively infected with ST-FeLV. St-FeLV is a subgroup AB retrovirus (Sarma, et al., supra). The CT600 leopard cat testicle cell line is available from Dr. Murray Gardner, University of California, Davis. This cell line was productively infected with CT600-FeLV, a subgroup A retrovirus (Rashud and Gardner, *J. National Cancer Institution* (1981) 67:929–933). H927 feline cells that had been productively infected with FeLV subgroup A, B, or C are available from Dr. Oswald Jarrett, University of Glasgow. These cell-lines were also maintained in MEM/L15 media with 10% fetal bovine serum.

Two murine lymphoid cell lines, HT-2C and CT6, proliferated in response to crude preparations of feline interleukin-2 (IL-2) and were used to assay for feline IL-2 by a standard proliferation assay (Gillis et al., *J. Immunol.* (1981) 120:2027–2032). Two additional cell lines, FT-I and FT-II, were used for some of the IL-2 assays. These were IL-2 dependent feline thymus cell lines that were originally derived from thymic explants of young kittens. Thymic explants were cultured in vitro in the presence of crude feline IL-2. After a number of passages the cells were cloned in the presence of IL-2. Both of these cell lines were totally dependent on exogenous IL-2 for growth in culture. These cell lines were maintained in RPMI 1640 or MEM/L15 media with 10% fetal bovine serum.

*Felis catus* 9 (Fc9) and Crandell feline kidney (Crfk) cell lines were initially obtained from Naval Biologics Laboratory, Oakland, CA and were used for the production of feline beta-interferon. The Fc9 and Crfk cells were maintained on MEM/L15 media containing 10% fetal bovine serum.

Clone 81 S+L- cells were obtained from Dr. Peter Fischinger, National Institutes of Health. These cells were used for determining the infectivity of FeLV by focus formation (Fischinger et al, *J. Virol.* (1974) 14:177–179).

Peripheral blood lymphocytes (PBLs) were obtained from the blood of adult specific pathogen free cats by Ficoll-Hypaque density centrifugation (Boyum, *Scand. J. Clin. Lab. Invest.* (1968) 21, Suppl. 97:77–88).

Peripheral blood lymphocytes were cultured in RPMI 1640 media containing 10% fetal bovine serum, 10 mM Hepes buffer, and 0.22% sodium bicarbonate. Cultures were incubated at 37° C. in a culture chamber containing 20% $CO_2$, 7% $O_2$, and 83% $N_2$ and agitated on a platform rocker at 4 cycles/min.

Lymphoid cell characterization. Feline cell surface markers were determined by indirect immunofluorescence assay (IFA) with rabbit antisera to feline immunoglobulins (IgG, IgM, IgA) and thymocytes, and by rosetting with guinea pig red blood cells (GP-RBC). Rabbit antiserum was preabsorbed with non-lymphoid feline cells (Crfk and FF 64/90) and cat erythrocytes. Rabbit anti-cat thymocyte serum was also preabsorbed with cat bone marrow cells. Pooled normal rabbit serum was used as a control to detect non-specific and Fc receptor-mediated adherence of the rabbit antiserum. Pooled normal rabbit serum, at the same antiserum dilutions used for the assay, did not cause surface fluorescence on any of the feline cells tested.

The IFA assay consisted of incubating feline cells with rabbit antiserum for 20 minutes at 37° C. The cells were washed twice with PBS and incubated for an additional 20 minutes at 37° C. with 1:25 dilution of fluorescein-conjugated goat anti-rabbit-IgG (Antibodies Incorporated, Davis, Calif.). The cells were then washed with phosphate buffered saline (PBS), pH 7.4, resuspended in 50% glycerol-PBS, and examined for surface fluorescence by UV microscopy.

Rosetting with GP-RBC to identify feline T lymphocytes was conducted according to the procedure of Taylor et al., (*J. Immunol.* (1975) 115:862–865). Briefly, cultured cells or PBL were suspended in Hank's buffered saline solution at a concentration of $4 \times 10^6$ cells/ml and incubated for 20 minutes at 37° C. with an equal volume of 1% suspension of GP-RBC. The cells were loosely pelleted at 600 rpm for 2 minutes and then incubated for an additional 40 minutes at room temperature. The pelleted cells were gently resuspended, stained with an equal volume of 0.5% methylene blue, and examined in a hemocytometer. A minimum of 150 viable cells were counted, and cells with three or more adherent GP-RBC were counted as a rosette.

FeLV infectivity assays. Culture supernatants from LSA lines were placed on normal feline (Crfk, Fc9) and Clone 81 cells grown in 96 well culture plates. The media was changed 3 days later and culture supernatants assayed for FeLV-27 from 5 to 14 days post infection. The effect of feline interferons on FeLV replication was performed with the following modifications: one day prior to FeLV inoculation the cells were incubated with 100 antiviral units/well of interferon. The cells were then washed and fed with fresh media just prior to being infected with FeLV. In some experiments, interferon preparations (100 U/well) were added with the fresh culture media at the time of infection. Infectious FeLV was also measured by focus formation on Clone 81 cells (Fischinger, et al., supra). The ability of the feline interferons to enhance or to suppress FeLV infectivity was manifested by an elevation or reduction in the numbers of foci induced in the culture.

Preparation of standard feline interferons. Disassociated cat spleen cells or peripheral blood lymphocytes from healthy adult specific pathogen free (SPF) cats were incubated with specific lymphokine inducers in 35 mm Falcon culture dishes or flasks at a density of $1 \times 10^6$ cells/ml. Cell viabilities were always above 90% as determined by trypan blue dye exclusion. Cells were maintained in culture as previously described.

Feline gamma interferon was induced by stimulating spleen cell cultures with Staphylococcal enterotoxin A (SEA) (Osborne et al., *Infect. Immun.* (1979) 23:80–86). Culture supernatants were harvested on day 3 at the peak of gamma-interferon production. Feline alpha-interferon was produced by Newcastle disease virus (NDV) infection of PBLs or vesicular stomatitis virus (VSV) infection of cat spleen cells and interferon containing culture supernatants were harvested on days 2 and 1, respectively. Feline beat-interferon was produced by infecting Fc9 or Crfk cells with NDV, and collecting culture supernatants after 24 hours.

Feline interferon assay. Feline interferon activity was assayed by a modification of a microplaque reduction method (Campbell et al. *Can. J. Microbiol.* (1975) 21:1247–1253), using approximately 40 plaque forming units (pfu) of VSV per well on Fc9 cells. One unit of interferon activity was defined as the amount required to decrease the number of plaques per well by 50%. Throughout the study, the same batch of SEA induced interferon was used as a reference for each assay. In addition, feline interferon was used as a reference for each assay. In addition, feline interferon was also assayed at times on Fc9 or Crfk cells using Sindbis virus. (Armstrong, *Applied Microbiol.* (1971) 21:723–725).

Characterization of feline interferons. Feline interferons were characterized on the basis of acid, heat, and sodium dodecyl suphate (SDS) sensitivities. To test for acid sensitivity, interferon preparations were adjusted to pH2 with 1 M HCl, incubated at 4° C. for 24 hours, and readjusted to pH 7.0 with HEPES buffer prior to being assayed. Heat treatment was at 56° C. for 30 minutes. Sodium dodecylsulfate sensitivity was measured by pretreating interferon preparations with 0.1% SDS for 2 hours at room temperature. Prior to being assayed, the mixture was diluted 1:1 with culture media to eliminate any direct toxic effect of SDS on the indicator cells.

Partial purification of feline interferons. Feline interferons were partially purified by procedures previously used for human interferons (Georgiades, *Texas Reports Biol. Med.* (1981) 41:179–183). Interferon containing solutions were concentrated with controlled pore glass beads (CPG) and then purified by Ultrogel AcA 54 chromatography. Interferon absorbed onto the CPG was eluted with 50% ethylene glycol (PEG) prior to gel filtration. PEG concentrated interferon preparations were applied to a 2.5×95 cm Ultrogel AcA 54 column equilibrated in 5% ethylene glycol, 1M NaCl in PBS (pH 7.0). The flow rate was 35 ml/hr and 5 ml fractions were collected and assayed for interferon activity. The column was calibrated with blue dextran (2,000,000 daltons), bovine albumin (67,000 daltons), ovalbumin (45,000 daltons), and cytochrome c (12,600 daltons). This two-step purification scheme yielded feline interferon preparations with specific activities of 1 to $5 \times 10^6$ units/mg in the peak fractions.

Sources of IL-2. Recombinantly produced human IL-2 (rIL-2) was provided by Cetus Corporation, Emeryville, CA. Crude IL-2 preparations were obtained from culture supernatants of ConA stimulated cat (CAFT) or rat spleen cells (RAFT). The CAFT and RAFT preparations contained approximately 300 IL-2 units/ml based on titration in H2-2C cells. Residual ConA in these crude preparations was inactivated by alpha-methylmannoside.

Feline IL-2 assay. The murine IL-2-dependent cell lines HT-2C and CI6 were found to proliferate in response to crude feline IL-2 preparations and could be used to assay for feline IL-2 using the method described for assaying human and mouse IL-2 (Gillis, et al., *J. Immunol.* (1978) 120:2027–2032). Test supernatants and IL-2 positive control supernatants (mitogen-stimulated cat cell cultures fluid) were incubated with $10^4$ HT-2C or CT6 cells/well in 96 well culture plates for 24 hours followed by an 18 hour pulse with 1–2 µCi of $^3$H-thymidine incorporation determined by standard scintillation techniques.

FeLV-gp70, -p27 and -p15E assays. All three of these FeLV structural proteins were quantitated by double sandwich type enyme linked immunosorbent assay (ELISA). The assay procedure for FeLV-p27 was identical to that described by Lutz et al., (*J. Immunol. Methods* (1983) 56:209–220). Similar assays were used for the quantitation of FeLV-gp70 and -p15E. The FeLV-gp70 assay utilized polyclonal goat anti-FeLV-gp70 and -p15E. The FeLV-gp70 assay utilized polyclonal goat anti-FeLV-gp70 immunoglobulin (NIH 815-210) for the "catcher"antibody and the 25-5D monoclonal mouse anti-FeLV-gp70 IgG conjugated to horse radish peroxidase (HPASE) for the second antibody. The ELISA for FeLV-p15E utilized the 29-2C monoclonal mouse anti-FeLV-p15E IgG as the "catcher" and the 29-2F monoclonal mouse anti-FeLV-p15E IgG conjugated to HPASE as the second antibody. Protein standards for the assays were purified on immunoaffinity columns made of Sepharose-4B coupled to mouse monoclonal IgG against the various FeLV proteins.

Characterization of LSA cells. The LSA cells, was confirmed by analysis of cell surface receptors, and comparison with a known feline T-lymphoblastoid cell line called FL74. The parent LSA-I cells and cells from the LSA-D4 and -D5 clones formed rosettes with guinea pig red blood cells and reacted with anti-cat thymocyte serum (Table I). The cell surfaces of LSA cells also lacked immunoglobulin receptors when reacted with anti-cat IgG, and IgM, and IgA serum. The FL74 cells reacted in an identical manner when tested for these same membrane markers (Table I).

LSA cells were tested for their ability to respond to various T-cell mitogens. As a comparison, FL74 lymphoblastoid cells were tested in a similar manner. LSA and FL74 cells both failed to proliferate after being exposed in culture to various concentrations of ConA, PHA, and SEA (Table II), and neither cell line could be stimulated to produce interferons or IL-2 (Table III). Feline IL-2 dependent thymocyte cultures (FT-I and FT-II) and mouse HT-2C cells, however, responded very well to exogenous IL-2 stimulation (Table IV). LSA cells, like FL74 reference cells, appeared, therefore, to be IL-2 independent but of T-cell origin.

TABLE I

The characterization of cell surface markers on normal feline peripheral blood lymphocytes (PBL's), FL74 lymphoblastoid cells, and on LSA-I, -D4, and -D5 thymic tumor cells. Normal cultured feline fibroblasts (Fc-9) were used as negative controls.

| Cell Surface Marker | Cell type | | | | | | |
|---|---|---|---|---|---|---|---|
| | PBL-I | PBL-2 | LSA-I | LSA-D4 | LSA-D5 | FL74 | Fc-9 |
| Guinea Pig RBC | | | | | | | |
| Rosettes/nonrosettes | 94/130 | 41/211 | 226/49 | 286/27 | 243/13 | 174/65 | 3/226 |
| (% rosette formation) | (42) | (19) | (82) | (91) | (95) | (73) | (1) |
| theta antigen (IFA)* | +++ | ++++ | +++++ | ++++ | ++++ | ++++ | neg. |
| (% fluorescing cells) | (42) | (53) | (91) | (94) | (95) | (97) | neg. |
| IgM (IFA)* | ++ | ++ | neg. | neg. | neg. | neg. | neg. |
| (% fluorescing cells) | (10) | (10) | (0) | (0) | (0) | (0) | (0) |
| IgG (IFA)* | ++ | + | neg. | neg. | neg. | neg. | neg. |
| (% fluorescing cells) | (17) | (6) | (0) | (0) | (0) | (0) | (0) |
| IgA (IFA)* | +/− | neg. | neg. | neg. | neg. | neg. | neg. |
| (% fluorescing cells) | (1) | (0) | (0) | (0) | (0) | (0) | (0) |

*+++++ total cell surface, ++++ ¾ cells surface, +++ ½ cells surface, ++ ¼ cell surface, + 3 patches, +/− 1 to 2 small patches

TABLE II

The proliferation response of normal feline peripheral blood lymphocytes (PBLs), LSA-I cells, and FL74 cells to the T-Cell mitogens Staphylococcal enterotoxin A (SEA), Conconavalin A (ConA), and Phytohemagglutinin (PHA).

| Cell Type | Mitogen (µg/ml) | | Cellular proliferation assayed by $^3$H—thymidine incorporation (cpm, x + SD) | | |
|---|---|---|---|---|---|
| | | | Day 2 in culture | Day 3 in culture | Day 4 in culture |
| PBL | SEA | (0.5) | 8,204 ± 2,798 | 18,655 ± 1,197 | not tested |
| | | (0.05) | 7,133 ± 1,438 | 14,504 ± 2,720 | not tested |
| | | (0.005) | 4,458 ± 804 | 17,530 ± 1,295 | not tested |
| | ConA | (5.0) | 9,520 ± 826 | 18,270 ± 1,665 | not tested |
| | | (2.5) | 7,844 ± 2,700 | 15,924 ± 2,155 | not tested |
| | PHA | (30) | 5,103 ± 891 | 10,599 ± 6,560 | not tested |
| | | (15) | 2,298 ± 154 | 10,818 ± 1,748 | not tested |
| | None | | 185 ± 29 | 8,495 ± 2,170 | not tested |
| LSA-I | SEA | (0.5) | 11,367 ± 996 | 14,251 ± 1,566 | 17,427 ± 2,020 |
| | | (0.05) | 9,511 ± 1,065 | 15,946 ± 1,399 | 26,373 ± 2,152 |
| | | (0.005) | 12,184 ± 1,550 | 16,193 ± 2,304 | 24,692 ± 3,356 |
| | ConA | (5.0) | 12,254 ± 1,461 | 13,228 ± 1,591 | 18,512 ± 3,154 |
| | | (2.5) | 10,380 ± 184 | 16,159 ± 1,795 | 26,482 ± 3,457 |
| | | (0.25) | 10,304 ± 923 | 13,664 ± 1,408 | 21,928 ± 509 |
| | PHA | (30) | 9,816 ± 683 | 7,680 ± 3,185 | 7,758 ± 710 |
| | | (15) | 7,667 ± 1,244 | 10,975 ± 3,272 | 16,144 ± 2,572 |
| | | (1.5) | 10,678 ± 1,489 | 10,004 ± 182 | 18,894 ± 1,286 |
| | None | | 11,026 ± 257 | 12,422 ± 4,356 | 18,508 ± 1,637 |
| FL74 | SEA | (0.5) | 57,462 ± 977 | 20,925 ± 3,510 | not tested |
| | | (0.05) | not tested | 24,000 ± 1,380 | not tested |
| | ConA | (5) | 42,575 ± 13,624 | 6,795 ± 440 | not tested |
| | | (2.5) | not tested | 12,029 ± 3,045 | not tested |
| | PHA | (30) | 55,172 ± 11,478 | not tested | not tested |
| | None | | 55,490 ± 4,556 | 48,029 ± 2,517 | not tested |

TABLE III

IL-2 and Interferon production by normal feline spleen cells, LSA-I, -D4, and -D5 cells, and FL74 cells cultured in the presence of T-cell mitogens.

| Cell type | Mitogen (µg/ml) | | IL-2 Production (cpm, x + SD) | | | Interferon Production (U/ml) | | |
|---|---|---|---|---|---|---|---|---|
| | | | Day 1 | Day 2 | Day 3 | Day 1 | Day 2 | Day 3 |
| spleen cells | SEA | (0.5) | 23,195 ± 4,606 | 26,325 ± 3,058 | 23,466 ± 966 | 58 | 215 | 250 |
| | ConA | (5.0) | 2,406 ± 325 | 1,458 ± 130 | 320 ± 26 | 20 | 30 | 200 |
| | PHA | (30.0) | 708 ± 146 | 2,899 ± 322 | 2,121 ± 86 | 25 | 40 | 200 |
| | None | | 274 ± 44 | 296 ± 21 | 607 ± 88 | 4 | 10 | 30 |
| LSA-I | SEA | (0.5) | 339 ± 20 | 380 ± 12 | 239 ± 15 | 15 | 100 | 400 |
| | ConA | (5.0) | 287 ± 23 | 342 ± 28 | 261 ± 24 | 15 | 100 | 400 |
| | PHA | (30.0) | 288 ± 37 | 322 ± 28 | 336 ± 63 | 15 | 100 | 400 |
| | None | | 265 ± 37 | 332 ± 30 | 314 ± 33 | 15 | 100 | 400 |
| LSA-D4 | SEA | (0.5) | 294 ± 71 | 281 ± 49 | 258 ± 13 | 200 | 3,000 | 20,000 |
| | ConA | (5.0) | 273 ± 31 | 290 ± 74 | 216 ± 27 | 200 | 3,000 | 20,000 |
| | PHA | (30.0) | 315 ± 44 | 325 ± 50 | 329 ± 91 | 200 | 3,000 | 20,000 |
| | None | | 401 ± 6 | 269 ± 27 | 228 ± 24 | 200 | 3,000 | 20,000 |
| LSA-D5 | SEA | (0.5) | 294 ± 2 | 357 ± 32 | 295 ± 23 | 80 | 400 | 3,000 |
| | ConA | (5.0) | 324 ± 47 | 279 ± 20 | 219 ± 4 | 80 | 400 | 3,000 |
| | PHA | (30.0) | 336 ± 72 | 261 ± 42 | 191 ± 14 | 80 | 400 | 3,000 |
| | None | | 246 ± 3 | 256 ± 5 | 149 ± 6 | 80 | 400 | 3,000 |
| FL74 | SEA | (0.5) | not tested | not tested | not tested | <3 | <3 | <3 |
| | ConA | (5.0) | not tested | not tested | not tested | <3 | <3 | <3 |
| | PHA | | not tested | not tested | not tested | <3 | <3 | <3 |

TABLE IV

The effect of exogenous IL-2 on the proliferation of normal feline PBL's, IL-2 dependent (FT-I and FT-II) and mouse thymocytes (HT-2C), and LSA-I, -D4 and -D5 cells.

| Cell Type | IL-2 Type | Il-2 Concentration | Cell Proliferation (Day 2 Harvest) $^3$H—Thymidine Incorporation (cpm) |
|---|---|---|---|
| Normal PBL | rIL-2 | 100 u/ml | 33,888 ± 2,539 |
| | | 10 | 3,034 ± 639 |
| | | 0 | 320 ± 82 |
| FT-I | rIL-2 | 200 u/ml | 2,181 ± 42 |
| | | 20 | 1,668 ± 469 |
| | | 2 | 1,954 ± 238 |
| | | 0 | 536 ± 286 |
| | RAFT | 1:3 | 831 ± 387 |
| | CAFT | 1:3 | 2,895 ± 496 |
| FT-II | rIL-2 | 200 u/ml | 5,513 ± 594 |
| | | 20 | 3,783 ± 357 |
| | | 2 | 1,902 ± 160 |
| | | 0 | 63 ± 18 |
| | RAFT | 1:3 | 600 ± 141 |

TABLE IV-continued

The effect of exogenous IL-2 on the proliferation of normal feline PBL's, IL-2 dependent (FT-I and FT-II) and mouse thymocytes (HT-2C), and LSA-I, -D4 and -D5 cells.

| Cell Type | IL-2 Type | Il-2 Concentration | Cell Proliferation (Day 2 Harvest) $^3$H—Thymidine Incorporation (cpm) |
|---|---|---|---|
| HT-2C | CAFT | 1:3 | 5,177 ± 428 |
|  | rIL-2 | 200 u/ml | 10,890 ± 1,485 |
|  |  | 20 | 14,825 ± 724 |
|  |  | 2 | 10,747 ± 1,434 |
|  |  | 0 | 611 ± 152 |
|  | RAFT | 1:3 | 10,007 ± 903 |
|  | CAFT | 1:3 | 9,670 ± 4,607 |
| LSA-I | rIL-2 | 200 u/ml | 9,570 ± 424 |
|  |  | 20 | 12,883 ± 889 |
|  |  | 2 | 11,430 ± 552 |
|  |  | 0 | 11,954 ± 1,045 |
|  | RAFT | 1:3 | 13,331 ± 2,218 |
|  | CAFT | 1:3 | 8,776 ± 1,010 |
| LSA-D4 | rIL-2 | 200 u/ml | 10,196 ± 2,619 |
|  |  | 20 | 8,842 ± 1,536 |
|  |  | 2 | 11,760 ± 773 |
|  |  | 0 | 10,531 ± 1,699 |
|  | RAFT | 1:3 | 11,170 ± 352 |
|  | CAFT | 1:3 | 9,202 ± 1,300 |
| LSA-D5 | rIL-2 | 200 u/ml | 9,207 ± 1,360 |
|  |  | 20 | 6,342 ± 1,858 |
|  |  | 2 | 7,727 ± 895 |
|  |  | 0 | 7,676 ± 2,225 |
|  | RAFT | 1:3 | 8,029 ± 29 |
|  | CAFT | 1:3 | 7,078 ± 2,531 |

Culture supernatants from normally dividing LSA and FL74 cells were assayed for activity against VSV and Sindbis virus infection of Fc9 feline fibroblast cells. Cultured LSA cells were found to constituitively produce large amounts of an anti-viral substance as evidenced by the anti-VSV and anti-Sindbis virus activity of culture supernatants (Table V). The culture media from FL74 cells, however, possessed no such anti-viral activity. The anti-viral activity of the LSA culture supernatants was found to be trypsin sensitive and to be effective on several cat cell lines and on canine MDCK cells, but was ineffective with mouse and human cells (Table V). The trypsin sensitivity, relative species specificity, and non-virus specificity of the LSA supernatant factor demonstrated that it was an interferon.

LSA cell culture supernatants were assayed for FeLV-p27 and for infectious FeLV. Culture fluids from LSA-1, -D4 and -D5 cells contained as much FeLV-p27 as culture fluids from FL74 cells, which were known to produce large amounts of whole infectious virus (Table VI). LSA culture fluids contained peak amounts of FeLV-p27 within 24 hours after passage and these levels were maintained for at least 5 days. Interferon production, however, slowly increased after passage and did not reach peak concentration until the 4th day. In addition to FeLV-p27, LSA and FL74 cell culture supernatants also contained FeLV-gp70 and -p15E (Table VI). Although FeLV-p27, -gp80 and -p15E were produced by LSA cells, very little infectious virus was present in LSA culture supernatants. Cell-free supernatants from LSA cells did not induce foci on Clone 81 cells (Table VII). In contrast, culture supernatants from FL74 cells induced numerous foci on the Clone 81 cells (Table VII).

TABLE V

Characterization of LSA and standard feline alpha-, beta-, and gamma-interferons according to virus and species specificity

| | Feline Interferon Type | | | |
|---|---|---|---|---|
| | LSA | PBL/NDV (alpha) | Crfk/NDV (beta) | Spleen/SEA (gamma) |
| VIRUS SPECIFICITY | | | | |
| Antiviral activity against: | | | | |
| Sindbis virus | + | + | + | + |
| VSV | + | + | + | + |
| SPECIES SPECIFICITY | | | | |
| Antiviral activity with various cell-lines: | | | | |
| Fc9 (cat) | + | + | + | + |
| Crfk (cat) | + | + | + | + |
| L-929 (mouse) | − | − | − | − |
| A549 (human) | − | − | − | − |
| MDCK (dog) | + | + | − | − |
| Trypsin Sensitivity | + | + | + | + |
| pH2 Sensitivity | + | − | − | + |

TABLE VI

The elaboration of FeLV-p27, -p15E, and -gp70 subunit proteins by LSA-I, -D4 and -D5 cells, FL74 lymphoblastoid cells, and normal feline fibroblasts (Fc9).

| Cell Source of Supernatant | FeLV Subunit Protein Expression as Measured by ELISA (OD units) | | |
|---|---|---|---|
| | FeLV-p27 | F-LV-p15E | FeLV-gp70 |
| LSA-1 | 466 | 450 | 60 |
| LSA-D4 | 414 | 289 | 42 |
| LSA-D5 | 345 | 449 | 31 |
| FL74 | 346 | 199 | 92 |
| Fc9 | 20 | 5 | 2 |

TABLE VII

A comparison of interferon and FeLV-p27 levels in the culture supernatants from various feline cell lines and the infectivity of the culture supernatants on Clone 81 and Crfk cells. Infectivity on Clone 81 cells was measured by focus induction and by the elaboration of FeLV-p27 after 7 days in culture. Infectivity on Crfk cells was measured by FeLV-p27 elaboration 7 days after being exposed to culture supernatants.

| | Culture supernatant | | | Infectivity of culture supernatant on Clone 81 cells | | Infectivity of culture supernatant on Crfk cell |
|---|---|---|---|---|---|---|
| | FeLV-p27 | Interferon | | FeLV-p27 production | | FeLV-p27 production |
| | ng/ml | μ/ml | Dilution | (ng/ml) | foci induction | (ng/ml) |
| LSA-1 | 447 | 100 | 1:4 | 80 | 0 | 39 |
| | | | 1:40 | 0 | 0 | 0 |
| LSA-D4 | 446 | 500 | 1:4 | 27 | 0 | 6 |
| | | | 1:40 | 0 | 0 | 0 |
| FF64/280 (FeLV AB) | 393 | 0 | 1:4 | 394 | + | 344 |
| | | | 1:40 | 298 | + | 316 |
| CT600 (FeLV A) | 238 | 0 | 1:4 | 362 | + | 344 |
| | | | 1:40 | 182 | + | 271 |
| H927/C (FeLV C) | 332 | 0 | 1:4 | 357 | + | 320 |
| | | | 1:40 | 230 | + | 259 |
| FL74 (FeLV ABC) | 453 | 0 | 1:4 | 170 | + | 185 |
| | | | 1:40 | 20 | + | 59 | virus as detected by clone 81 cells. As a cross check for infectious virus, culture supernatants from the clone 81 culture were infected onto normal feline fibroblast cell (Fc9). Supernatants from these secondary cultures were assayed for FeLV-p27 on days 7 and 12 (Table VIII). Only culture supernatants from clone 81 cells exposed to LSA-MA, -MC and-MG cultures contained detectable levels of infectious FeLV.

TABLE VIII

A comparison of FeLV-p27 elaboration and interferon production by various subclones of LSA-1 cells and infectivity in Clone 81 and normal feline fibroblasts (Fc9). Focus induction on Clone 81 cells was assayed 12 days after exposure and FeLV-p27 elaboration in Clone 81 and Fc9 cells was measured 7 days after cultures were exposed to supernatants from LSA cells

| | Cultures supernatant | | Infectivity of culture supernatants on: | | |
|---|---|---|---|---|---|
| | FeLV-p27 | Interferon | Clone 81 cells | | Fc9 Cells |
| LSA Subclones | (ng/ml) | (U/ml) | FeLV-p27 (ng/ml) | Focus induction | FeLV-p27 (ng/ml) |
| LSA -MA | 417 | <3 | 136 | ± | 93 |
| -MC | 383 | <3 | 132 | ± | 63 |
| -ME | 254 | 200 | 47 | ± | 25 |
| -MG | 344 | 100 | 217 | ± | 56 |
| MI | 403 | <3 | 11 | — | 1 |
| -MK | 327 | 10 | 43 | ± | 4 |
| LSA -D4A | 227 | 2,500 | 2 | — | 19 |
| -D4C | 215 | 3,000 | <1 | — | <1 |
| -D4E | 312 | 100 | <1 | — | 2 |
| -D4G | 302 | 1,000 | <1 | — | 1 |
| -D4I | 204 | 20,000 | 2 | — | <1 |
| -D4K | 239 | 5,000 | <1 | — | <1 |
| LSA -D5A | 259 | 600 | <1 | — | <1 |
| -D5C | 244 | 100 | <1 | — | 4 |
| LSA -D5E | 149 | 200 | <1 | — | <1 |
| -D5G | 177 | 100 | <1 | — | <1 |
| -D5I | 292 | 3,000 | <1 | — | <1 |
| -D5K | 254 | 3,000 | <1 | — | <1 |

The LSA-I cells appeared to produce defective FeLV particles. The relationship between interferon and virus production was studied by cloning the original LSA-I cells into high and low interferon producing cell-lines. The LSA-D4 and -D5 clones and subclones produced high levels of both interferon and FeLV-p27 (Table VIII). When culture supernatants from these various clones of the original LSA-I cell line were tested on Clone 81 cells, only the LSA-MA, -MC, -ME, -MG, and-MK supernatants demonstrated infectious Characterization of LSA interferon. The interferon produced by the LSA-D4 and-D5 cell lines was compared with known classes of feline interferons. These characterized interferons include alpha interferon produced by VSV infected cat spleen cells and peripheral blood, beta-interferon produced by NDV infected feline fibroblasts (Crfk), and gamma interferon produced by stimulated cat spleen cells.

All three classes of recognized feline interferons and LSA interferon were tested for heat, acid, and SDS stability (Table IX). The LSA interferon was acid labile, and SDS and heat stable. The alpha- and beta-interferons were not effected by heat, acid, and SDS treatment. The gamma-interferon preparation was acid, SDS, and heat labile.

TABLE X

The effect of purified LSA and standard feline beta- and gamma-interferons on the mitogen induced proliferation of feline peripheral blood lymphocytes.

| Interferon type | % Interferon containing culture fluid in wells | Mitogen induced proliferation, $^3$H—thymidine incorporation (cpm $\bar{x}$ + SD) (% Control) | | | |
|---|---|---|---|---|---|
| | | SEA | CON A | PHA | PWM |
| LSA[a] (Purified) | 25 | 3,370 ± 771 (30) | 5,744 ± 482 (47) | 1,522 ± 288 (13) | 1,158 ± 53 (20) |
| | 10 | 5,265 ± 1,181 (48) | 11,402 ± 2,786 (93) | 4,216 ± 1,193 (35) | 4,165 ± 1,330 (71) |
| | 5 | 8,630 ± 793 (78) | 12,700 ± 362 (104) | 5,138 ± 342 (43) | 3,925 ± 1,286 (67) |
| | 0.5 | 10,827 ± 1,256 (98) | 11,022 ± 1,624 (90) | 4,618 ± 1,969 (39) | 5,091 ± 973 (87) |
| Mock[b] | 25 | 9,633 ± 845 (87) | 13,195 ± 2,964 (108) | 8,074 ± 643 (67) | 3,2274 ± 306 (56) |
| | 10 | 11,018 ± 874 (100) | 15,992 ± 1,381 (131) | 12,183 ± 3,952 (102) | 5,122 ± 285 (88) |
| | 5 | 11,226 ± 978 (101) | 15,067 ± 2,344 (123) | 10,271 ± 1,988 (86) | 5,289 ± 1,014 (91) |
| Gamma | 25 | 831 ± 379 (8) | 489 ± 221 (2) | 303 ± 118 (3) | 2,154 ± 232 (37) |
| | 10 | 9,019 ± 1,370 (82) | 8,870 ± 1,910 (73) | 3,933 ± 226 (33) | 4,446 ± 212 (76) |
| | 5 | 12,041 ± 327 (109) | 12,303 ± 649 (101) | 4,971 ± 355 (42) | 4,598 ± 1,225 (79) |
| | 0.5 | 10,719 ± 904 (97) | 14,044 ± 660 (115) | 8,005 ± 1,467 (67) | 5,171 ± 1,069 (89) |
| Beta | 25 | 45 ± 12 (0.4) | 84 ± 7 (1) | 76 ± 20 (1) | 56 ± 3 (1) |
| | 10 | 1,287 ± 757 (117) | 610 ± 302 (5) | 560 ± 254 (5) | 675 ± 385 (12) |
| | 5 | 10,764 ± 1,285 (98) | 7,341 ± 1,861 (60) | 7,763 ± 202 (65) | 5,176 ± 842 (89) |
| | 0.5 | 8,076 ± 1,700 (73) | 11,286 ± 561 (92) | 10,466 ± 667 (88) | 4,264 ± 440 (73) |

[a]25% mixture contained approximately 100 U of interferon activity.
[b]Mock preparation consisted of culture medium that had undergone the same purification scheme as the LSA, gamma-, and beta-interferons.

As a next step, LSA interferon and the standard feline alpha-, beta-, and gamma-interferons were characterized by Ultrogel AcA 54 chromatography. The peak of the LSA interferon activity was detected at 20,000 daltons, whereas the feline gamma-, beta-, and alpha-interferons eluted at 17–19,000, 19–25,000 and 25–45,000 daltons, respectively.

Unlike the LSA interferon, which eluted as a very sharp peak from the gel column, the standard feline alpha-, beta-, and gamma-interferons eluted as broad peaks of protein, sometimes forming several merging peaks of activity. This was in keeping with the heterogenous nature of these interferon classes in other species. In the case of the interferons induced by VSV stimulation of cat spleen cells, two widely separated peaks of activity were observed at 19,000 and 29,000 daltons. These two interferons were probably alpha and beta.

Biologic activities of LSA interferon. Partially purified LSA interferon had additional biological properties that resembled standard acid stable alpha- and beta-interferons. LSA interferon, as well as alpha- and beta-interferon, suppressed the mitogen induced blast cell response of normal feline peripheral blood lymphocytes by 50% or more.

LSA and the standard alpha and beta feline interferons were next compared for their ability to suppress FeLV infection in vitro. All three types of interferons suppressed FeLV (FL74) induced focus formation on Clone 81 cells (Table XI). Although there was a marked suppression in the numbers of FeLV induced foci on interferon pretreated Clone 81 cells, the levels of FeLV-p27 in Clone 81 culture supernatants was as high as was similarly infected cultures that had not been pretreated with the various feline interferon preparations (Table XI).

TABLE XI

The effect of LSA and standard feline interferons on FeLV infection of Clone 81 and Crfk cells. Focus induction on Clone 81 cells was scored on day 7 after interferon treatment and FeLV exposure, while FeLV-p27 elaboration in clone 81 and Crfk cells was measured on day 5.

| Interferon Treatment | FeLV* Exposure | Infectivity on: | | Crfk Cells |
|---|---|---|---|---|
| | | Clone 81 Cells | | |
| | | FeLV-p27 (ng/ml) | foci | FeLV-p27 (ng/ml) |
| LSA | + | 272 | — | 167 |
| gamma (SEA spleen) | + | 204 | — | 105 |
| alpha/beta (VSV spleen) | + | 213 | — | 138 |
| none | + | 161 | ++ | 99 |
| none | — | 0 | — | 0 |

*cultures exposed to FL74 tissue culture fluid containing approximately 100 ng/ml FeLV (FL74).

Preliminary studies characterizing the LSA viral particles

Virus particles produced by LSA-1 cells (or subclones) appeared different on electron micrographs from particles produced by LSA-MA cells (a non-interferon producing subclone of LSA-1 cells that produces infectious virus). The nucleoids appeared less dense, and many of the particles were smaller than normal and resembled the surface antigen particles of human hepatitis-B virus. When analyzed and compared with infectious LSA-MA particles, LSA-1 virus contained a greater concentration of envelope (gp70) and core (p27) proteins (Table XI). Reverse transcriptase was present in both LSA-1 and LSA-MA particles in an active form and at a normal concentration. LSA-1 virus, however, appeared to be deficient in RNA (Table XI). These findings were similar to those described for hepatitis-B virus surface antigen particles (Gerin: Isolation and Physiochemical Characterization of HBAG, In: Vyas et al., (ed.): Hepatitis and Blood Transfusion, N.Y. Grune and Stratton, 1972, pp. 205–219.

TABLE XII

A comparison of noninfectious
LSA-and infectious MA-FeLV virions

| | MA-FeLV (infectious) | LSA-FeLV (noninfectious) |
|---|---|---|
| Bouyant density | 1.1468 g/cm$^3$ | 1.1465 g/cm$^3$ |
| Reverse transcriptase | 540 cpm/μg TP | 582 cpm/μg TP |
| RNA | 0.212 μg/μg TP | 0.098 μg/μg TP |
| p27 | 0.177 μg/μg TP | 0.975 μg/μg TP |
| gp 70 | 0.131 μg/μg TP | 0.478 μg/μg TP |

The relative deficiency of RNA in LSA-1 virions was also apparent from electron microscopic studies. Virus buds were almost impossible to visualize because of the absence of the dense membrane accumulations of RNA in the area where the virions form. The nucleoids of immature and mature particles were also less intensely stained.

LSA-1 virions were noninfectious in cell-culture (Table VII). Susceptible cat cells infected with large amounts of LSA-1 virus also did not induce foci on clone 81 S+L- cells. Fresh tissue culture media containing LSA-1 virus, when given intraperitoneally in volumes as great as 50 mls, was totally noninfectious to adolescent cats. Cats given this material never became viremic as determined by testing for viral antigen by indirect fluorescent antibody (IFA) staining of blood cells, serum ELISA for FeLV-p27, or virus isolation by cell culture of peripheral blood leukocytes or bone marrow. Moreover, latent FeLV virus could not be reactivated by treating these cats with large doses of methylprednisolone. Methylprednisolone readily activates FeLV in latently infected cats (Feline Practice, 14(2):32-48).

To further study whether LSA-1 virus was totally inactivated, 6 newborn kittens were inoculated intraperitoneally with 1 ml of LSA-1 tissue culture fluid. Blood was taken from the kittens at weekly intervals for 12 weeks and was assayed for virus. Newborn kittens inoculated with LSA-1 tissue culture fluid developed good antibody responses by 4 to 6 weeks of age, but were never detectably viremic. The possibility that the interferon contained in the inoculum had "interfered" with the infectivity of LSA-1 virus was also tested by inoculating 3 other newborn kitten and cultured cat cells with pelleted and washed virus from LSA-1 tissue culture fluid. Interferon free inocula containing LSA-1 virus was not infectious to either newborn kittens or to cat cells in culture. LSA-1 virus was, therefore, noninfectious even in the absence of interferon.

Efficacy of LSA-1 vaccine in preventing persistent FeLV infection in cats

Cats that were inoculated intramuscularly with LSA-1 vaccine had poor IFA antibody responses with only 2/6 cats developing titers of 1:5 or greater (Table XII). Five out of six cats inoculated intraperitoneally, however, developed IFA antibody titers of 1:5 or greater. After challenge-exposure with virulent FeLV, 3/6 kittens vaccinated intramuscularly became persistently viremic compared to 1/6 kittens vaccinated intraperitoneally (Table XII). In contrast, 5/6 nonvaccinated littermate kittens became persistently infected after challenge-exposure. It appeared, therefore, that IM immunizations were not as efficacious as IP immunizations. The vaccine trials were conducted, therefore, with a combination of IM and IP vaccination or with IP vaccination alone (Table XIII).

TABLE XII

Antibody response and protective immunity evoked by intramuscular versus intraperitoneal LSA-1 vaccination

| Group | Cat # | IFA antibody titer (reciprocal of serum dilution) weeks post initial immunization* | | | | | Persistent Viremia After challenge exposure |
|---|---|---|---|---|---|---|---|
| | | 0 | 3 | 5 | 7 | 10 | |
| Nonvaccinate | 3177 | 0 | 0 | 0 | 0 | 0 | + |
| | 3181 | 0 | 0 | 0 | 0 | 5 | + |
| | 3184 | 0 | 0 | 0 | 0 | 5 | − |
| | 3187 | 0 | 0 | 0 | 0 | 5 | + |
| | 3191 | 0 | 0 | 0 | 0 | 0 | + |
| | 3193 | 0 | 0 | 0 | 0 | 5 | + |
| IM vaccinates | 3176 | 0 | 0 | 0 | 0 | 20 | − |
| | 3179 | 0 | 0 | 0 | 0 | 5 | + |
| | 3182 | 0 | 0 | 0 | 0 | 10 | + |
| | 3185 | 0 | 0 | 5 | 5 | 10 | − |
| | 3188 | 0 | 0 | 5 | 10 | 20 | − |
| | 3190 | 0 | 0 | 0 | 0 | 20 | + |
| IP vaccinates | 3178 | 0 | 0 | 5 | 5 | 40 | − |
| | 3180 | 0 | 0 | 5 | 5 | 20 | − |
| | 3183 | 0 | 0 | 5 | 10 | 20 | − |
| | 3186 | 0 | 0 | 0 | 0 | 10 | + |
| | 3189 | 0 | 0 | 5 | 20 | 80 | − |
| | 3192 | 0 | 0 | 5 | 20 | 80 | − |

*Vaccinates given at weeks 0 and 3
**Persistent viremia measured 6 weeks post-challenge-exposure. Challenge-exposure with virulent FeLV administered during week 7 post-initial immunization.

Thirty-two 9-to-16 week old kittens were immunized with LSA-1 tissue culture fluid. The dose, vaccination regimen, and clinical outcome following challenge are given in Table XIII. Twenty-nine sibling animals were not vaccinated and served as controls for the study. Two weeks after the final vaccination both vaccinated and unvaccinated cats were challenge-exposed with virulent FeLV. Blood was collected weekly and assayed for the presence of viral antigens. The outcome of experimental infection is summarized in Table XIII. The rate of persistent FeLV infection post-challenge-exposure was 16% in vaccinated cats and 86% in non-vaccinated cats. Protection was better in cats given 2 or more mls per dose of vaccine that in cats given 1 ml (93% non-vaccinates vs 7% vaccinates in cats given 2 or more mls, and 77% vs 23% in cats given 1 ml).

TABLE XIII

Efficacy of LSA vaccine in preventing persistent FeLV infection in cats

| vaccine group | vaccine dose | Route of immunization | | | Outcome of challenge-exposure* | | | |
| | | 1st dose | 2nd dose | 3rd dose | nonvaccinates | | vaccinates | |
| | | | | | Persistent viremia | non-viremic | Persistent viremia | non-viremic |
|---|---|---|---|---|---|---|---|---|
| 58 | 2 ml | IM | IM | IP | 5 | 2 | 1 | 9 |
| 60A | 1 ml | IP | IP | IP | 5 | 0 | 1 | 4 |
| 60B | 5 ml | IP | IP | IP | 5 | 0 | 0 | 5 |
| 61A | 1 ml | IM | IP | | 5 | 1 | 2 | 4 |
| 61B | 1 ml | IP | IP | | 5 | 1 | 1 | 5 |
| | | | | TOTAL | 25 (86%) | 4 (14%) | 5 (16%) | 27 (84%) |

*400,000 ffu's CT600-FeLV oronasally on days 21, 23, 25 and 28 post-final vaccination, and 5 mg/kg methyl-prednisolone IM on day 28 post-vaccination Previous FeLV vaccines have generally not prevented infection, but rather altered the natural course of the virulent disease once it occurred (Pedersen et al., Am. J. Vet. Res., 40:1120–1126). To see if this was occurring in cats vaccinated with LSA-1, bone marrow was collected one week after challenge-exposure and cultured in vitro. The rationale for this study was as follows: if the infection was prevented altogether the bone marrow cultures would be negative, and if the course was merely altered, 1 week cultures would be virus positive. Culture supernatants were assayed weekly for FeLV. The virus was recovered from bone marrow in 4/22 vaccinates and 20/22 non-vaccinates. Recoveries of virus from vaccinated cats was always in animals that ultimately became persistently viremic following challengeexposure to virulent FeLV. These cats were usually the ones who failed to respond to the vaccine with IFA antibody titers of 1:5 or greater (Table XII). The event suggested that the properly immunized cats were solidly immune to infection, i.e. the vaccine did not merely alter the course of the infection.

It is evident from the above results that vaccines can be obtained by growing certain types of retroviruses in host cells in the presence of interferon, either endogenous or exogenous. Thus, it is found that the interferon acts to disrupt a late stage of the proliferative cycle of the virus, resulting in the production of envelope proteins, in conjunction with defective RNA. Furthermore, it is found that the resulting defective virus particles do not appear to complement each other, so that upon infection into a host, an infectious virus is formed. The subject method also provides a novel alpha-type feline interferon, which can be used for the production of feline retroviral vaccines or the treatment of infected hosts, both in vitro and in vivo, to inhibit viral proliferation.

Although the foregoing invention has been described in some detail by way of illustration and will be obvious that certain changes and modifications may be practiced within the scope of the appended claims.

What is claimed is:

1. A method for producing a retroviral vaccine form a B-type or C-type retrovirus, said method comprising:
   growing mammalian host cells infected with said retrovirus in the presence of interferon for a sufficient time for incompetent retrovirus particles to bud from said cells; and
   harvesting said retrovirus particles for use as a vaccine.

2. A method according to claim 1, wherein said interferon is present in at least 100U/ml and is alpha-interferon.

3. A method according to claim 2, wherein said alpha-interferon is acid labile alpha-interferon.

4. A method according to claim 1, wherein said interferon is constitutively produced alpha-type interferon and said host cells are T-cells.

5. A method for producing a retroviral vaccine from a C-type retrovirus, said method comprising:
   growing mammalian host lymphocyte cells infected with said retrovirus in the presence of at least 100U/ml alpha-interferon for a sufficient time for incompetant retrovirus particles to bud from said cells; and
   harvesting said retrovirus particles for use as a vaccine.

6. A method according to claim 5, wherein said retrovirus is feline leukemia virus.

7. A method according to claim 6, wherein said host cells are feline T-cells.

8. A method according to claim 5, wherein said alpha-interferon is alpha-type acid labile interferon constitutively produced by said host lymphocyte cells.

9. A method according to claim 5, wherein said alpha-interferon is added to said cells.

* * * * *